United States Patent [19]

Hatori et al.

[11] Patent Number: 4,464,467
[45] Date of Patent: Aug. 7, 1984

[54] ANTITUMOR ANTIBIOTICS PRODUCED BY NEW STREPTOMYCES

[75] Inventors: Masami Hatori, Yokosuka; Hiroaki Ohkuma, Tokyo; Masataka Konishi, Kawasaki; Takeo Miyaki, Yokohama; Hiroshi Kawaguchi, Tokyo, all of Japan

[73] Assignee: Bristol-Myers Company, New York, N.Y.

[21] Appl. No.: 401,469

[22] Filed: Jul. 26, 1982

[51] Int. Cl.³ .................. C12P 17/18; C12N 1/20; C12R 1/465
[52] U.S. Cl. .................. 435/119; 435/253; 435/886
[58] Field of Search .......... 435/119, 253, 886

[56] References Cited

U.S. PATENT DOCUMENTS 4,049,497 9/1977 Umezawa et al. .......... 435/119
4,105,658 8/1978 Umezawa et al. .......... 435/119

FOREIGN PATENT DOCUMENTS 131791 8/1982 Japan .

OTHER PUBLICATIONS

J. Antibiotics 29(1): 93–96, (1976).
J. Antibiotics 30(4): 340–343, (1977).
Symposium Papers of the 24th Symposium on the Chemistry of Natural Products (Osaka Japan), Oct. 13–16, 1981, paper #72, pp. 552–559.
J. Antibiotics 25(8): 437–444, (1972).
Chem. Pharm. Bull. 19(11): 2289–2293, (1971).
J. Antibiotics 25: 437, (1972).
Chem. Pharm. Bull. 19: 2289, (1971).
J. Am. Chem. Soc. 87: 5791, (1965).
J. Antibiotics 33 (6): 665–667 (1980).
J. Antibiotics 27 (11): 866–873 (1974).
J. Antibiotics 25 (11): 668–673 (1972).
J. Antibiotics 30 (5): 349–370 (1977).

Primary Examiner—Alvin E. Tanenholtz
Attorney, Agent, or Firm—David M. Morse

[57] ABSTRACT

A novel antitumor antibiotic designated herein as BBM-2040 is produced by fermentation of Streptomyces sp. strain J576-99 (ATCC 39143). BBM-2040, which may be recovered from the fermentation broth in either a desmethanol (BBM-2040B) or methanol-adduct (BBM-2040A) form, inhibits gram-positive and acid-fast bacteria and inhibits the growth of tumors such as P388 leukemia in mice.

3 Claims, 6 Drawing Figures

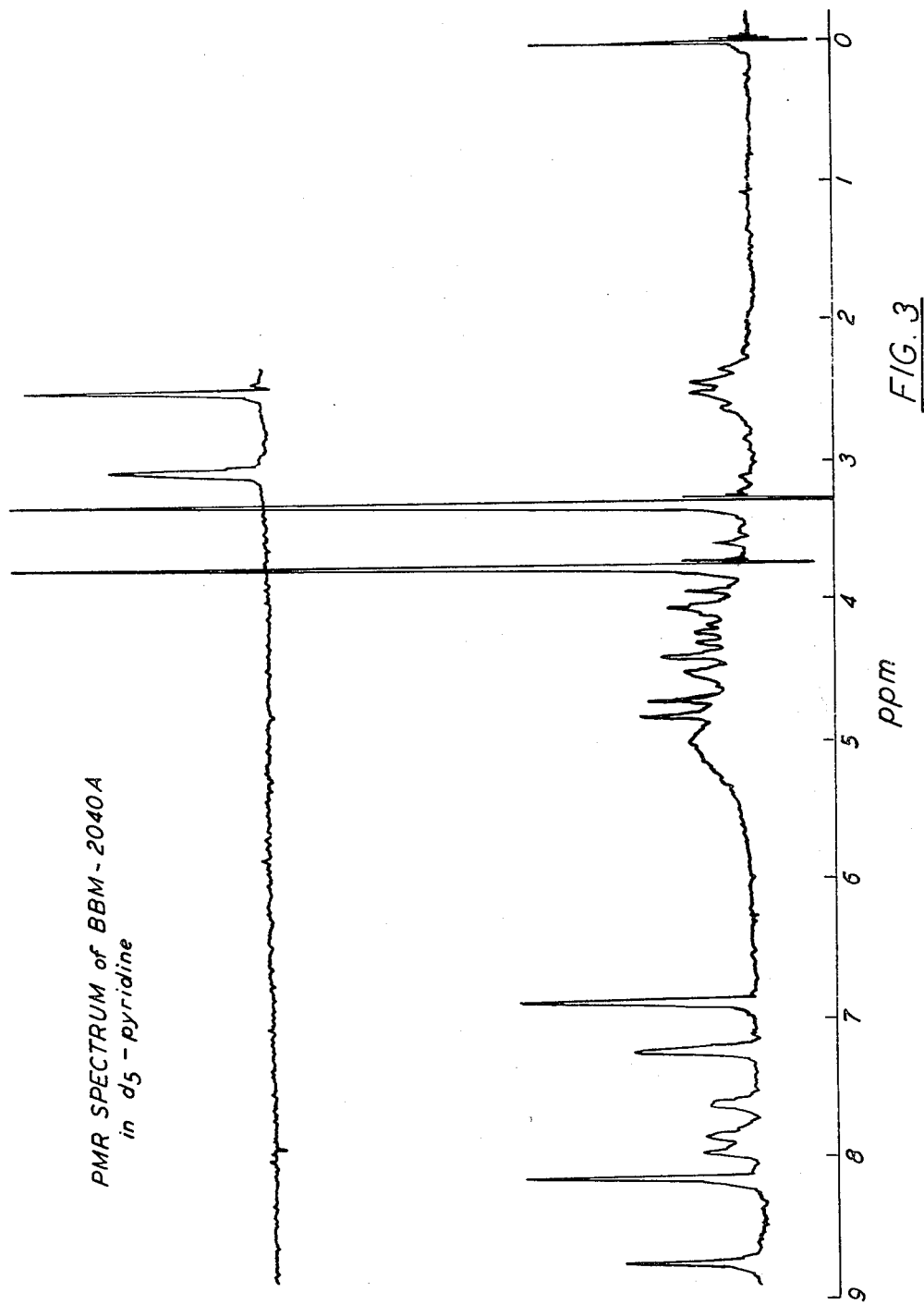

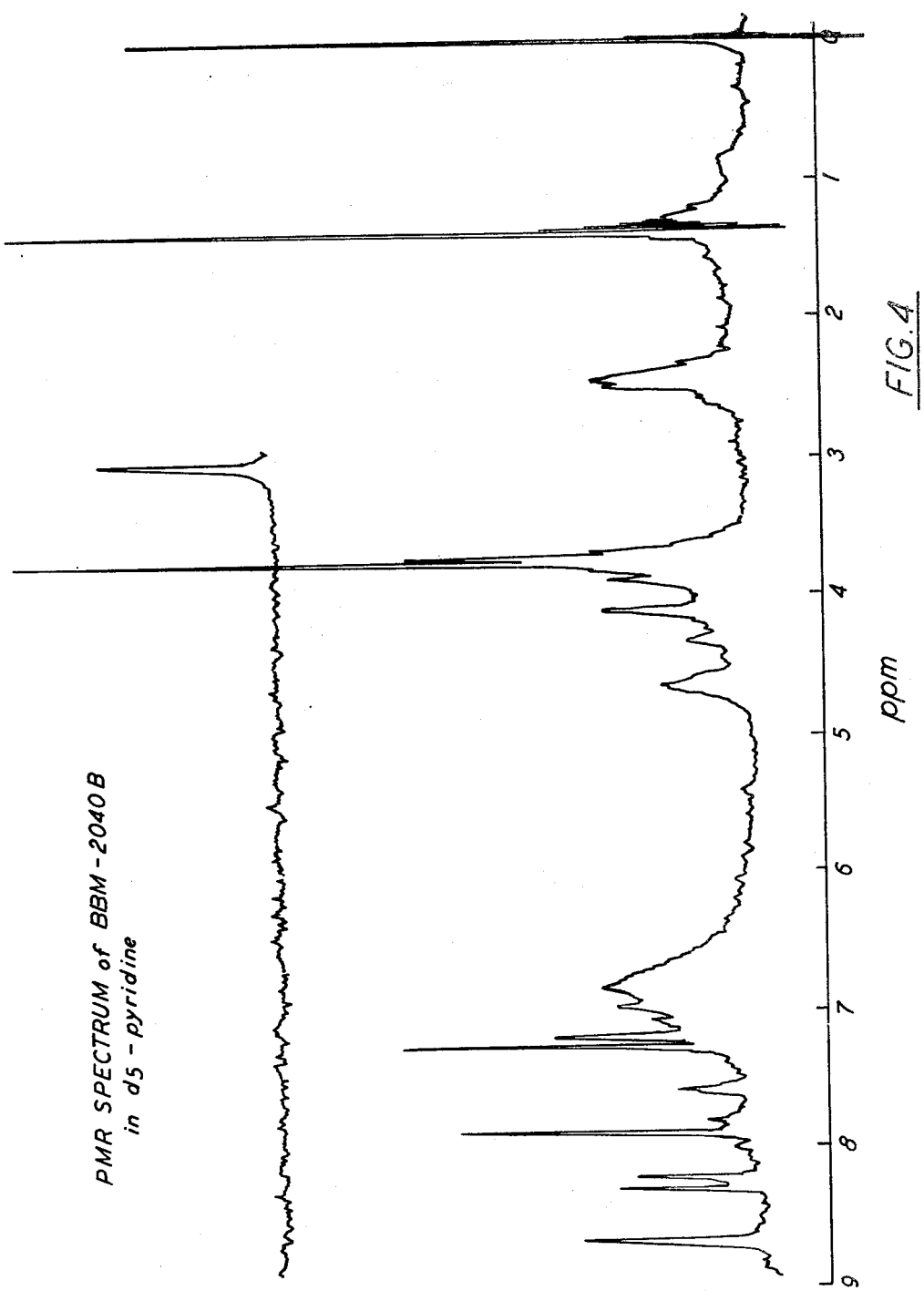

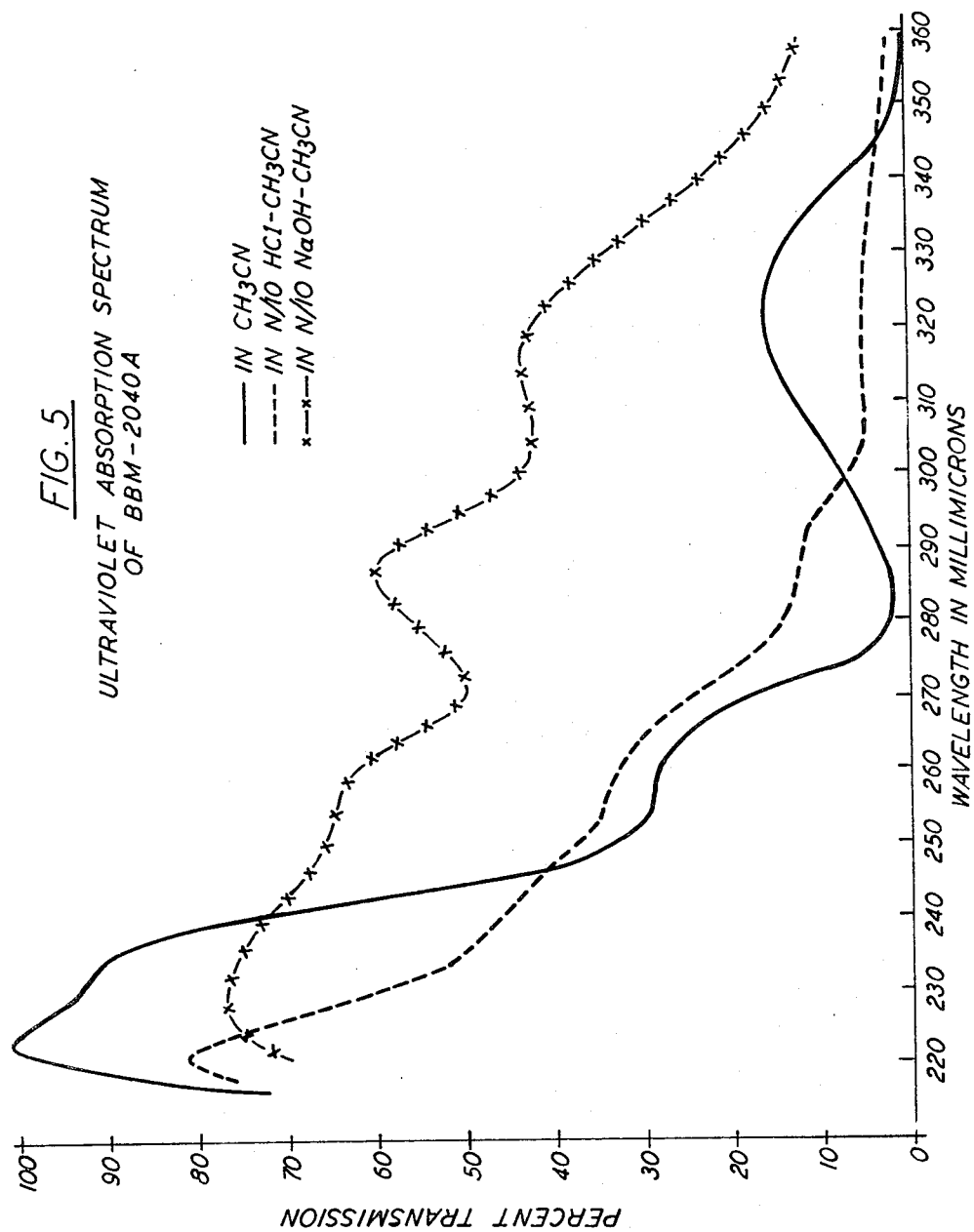

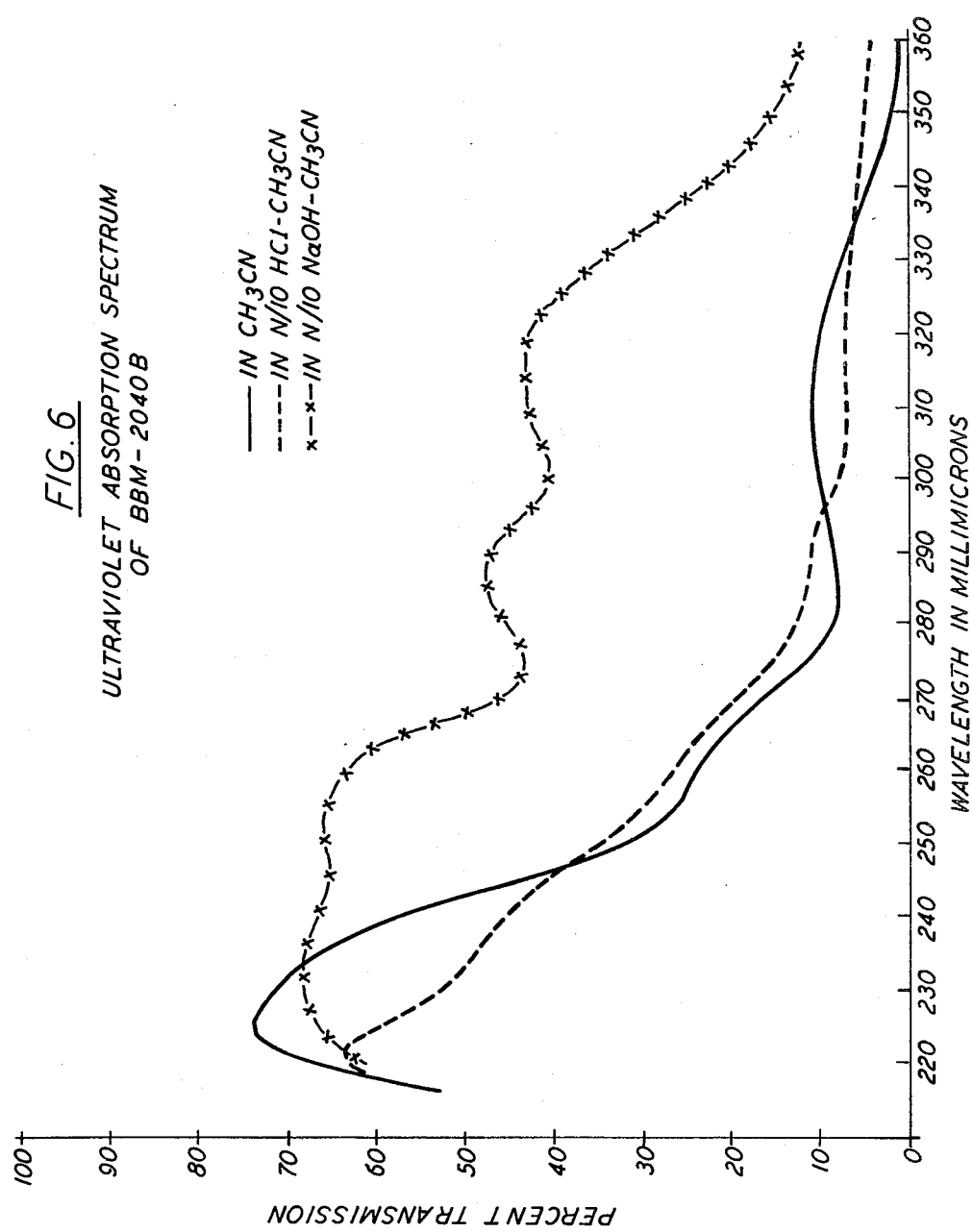

ANTITUMOR ANTIBIOTICS PRODUCED BY NEW STREPTOMYCES

BACKGROUND OF THE INVENTION (1) Field of the Invention

This invention relates to novel pyrrolo[2,1-c][1,4]benzodiazepin-5-one compounds having antibacterial and antitumor activity and to their production by fermentation of a new microorganism.

(2) Description of the Prior Art

The antitumor antibiotics of the present invention are new members of the anthramycin-neothramycin group of antibiotics.

The antitumor antibiotics, neothramycin A and neothramycin B, are disclosed in *J. Antibiotics* 29(1): 93–96 (1976) and *J. Antibiotics* 30(4): 340–343 (1977) as having the structures

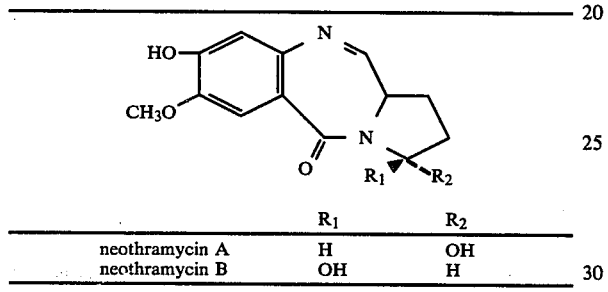

|  | R₁ | R₂ |
| --- | --- | --- |
| neothramycin A | H | OH |
| neothramycin B | OH | H |

The antibiotic BBM-2040B of the present invention may be structurally differentiated from the neothramycins in the position of its hydroxyl group.

The diastereoisomers of BBM-2040A and B of the present invention have been disclosed in *Symposium Papers of the 24th Symposium on the Chemistry of Natural Products* (Osaka, Japan, Oct. 13–16, 1981): Paper #72, pp. 552–559. Compounds 31b and 32b in this paper have the structures

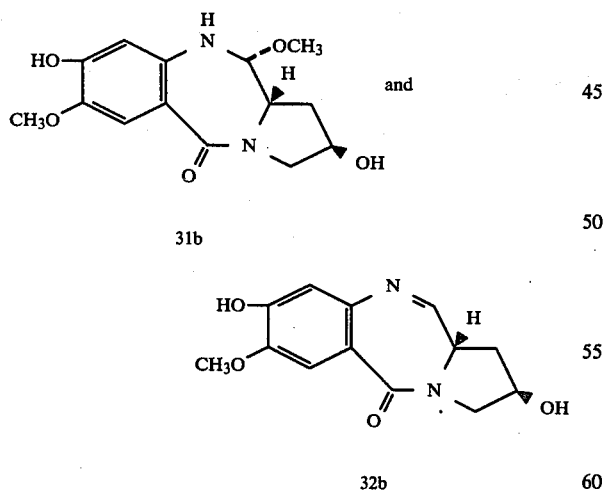

and may be differentiated from BBM-2040A and B of the present invention in the configuration of the C-2 hydroxy group, i.e. BBM-2040A and B have the C-2 hydroxy group in the α-configuration while the corresponding 31b and 32b diastereoisomers have the β-configuration at the C-2 hydroxy group. The present inventors have found that the β-hydroxy isomers described in the reference are essentially devoid of antitumor activity in the P388 mouse leukemia test while the α-hydroxy isomers claimed in the present application have a marked activity against P388 mouse leukemia in this same screening test.

The antitumor antibiotic, tomaymycin, is disclosed in *J. Antibiotics* 25(8): 437–444 (1972) and *Chem. Pharm. Bull* 19(11): 2289–2293 (1971) as being obtained by fermentation of *Streptomyces achromogenes* var. *tomaymyceticus*. Tomaymycin, which has the structure

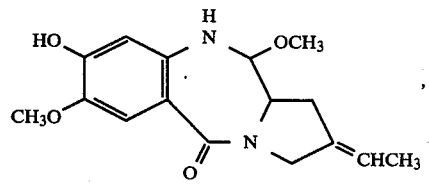

may be differentiated from BBM-2040A by the presence of the ethylidene group at the C-2 position.

The antitumor antibiotic, pretomaymycin, is disclosed in *J. Antibiotics* 25: 437 (1972) as having the structure

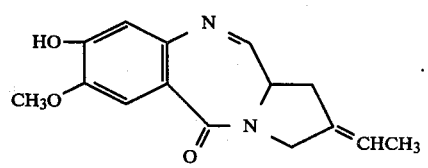

Pretomaymycin may be differentiated from BBM-2040B by the ethylidene group at the C-2 position.

The antitumor antibiotic, oxotomaymycin, having the formula

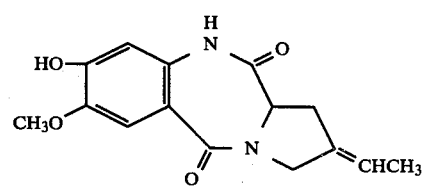

is disclosed in *Chem. Pharm. Bull.* 19: 2289 (1971). Oxotomaymycin differs from the BBM-2040 antiboiotics in the presence of the 2-ethylidene group and the presence of the carbonyl group at C-11.

Among the members of the anthramycin group of antitumor antibiotics are anthramycin having the formula

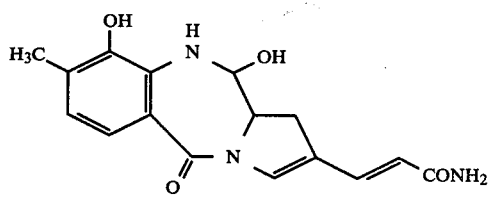

which is disclosed in *J. Am. Chem. Soc.* 87: 5791 (1965), mazethramycin having the formula

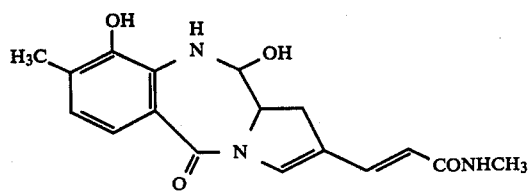

which is disclosed in *J. Antibiotics* 33(6): 665–667 (1980) and sibiromycin of the formula

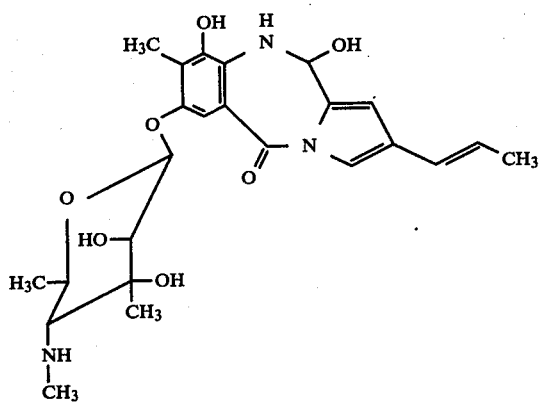

which is disclosed in *J. Antibiotics* 27(11): 866–873 (1974) and *J. Antibiotics* 25(11): 668–673 (1972).

An extensive comparison of anthramycin, tomaymycin and sibiromycin is found in *J. Antibiotics* 30(5): 349–370 (1977).

SUMMARY OF THE INVENTION

There is provided by the present invention a new pyrrolobenzodiazepine antibiotic designated herein as BBM-2040, said antibiotic being prepared by cultivating a new strain of Streptomyces designated Streptomyces sp. strain J576-99 (ATCC 39143) in an aqueous nutrient medium containing assimilable sources of carbon and nitrogen under submerged aerobic conditions until a substantial amount of BBM-2040 is produced by said organism in said culture medium and then recovering the BBM-2040 antibiotic from the culture medium.

The new BBM-2040 antibiotic of the present invention may be recovered from the fermentation broth either as a methanol-adduct form of the structure

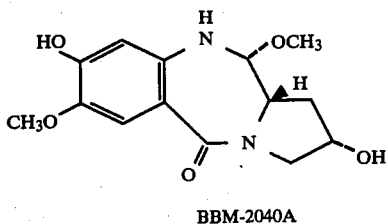

BBM-2040A or as the originally formed desmethanol form of the structure

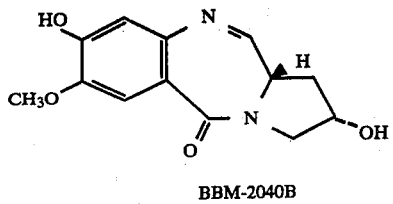

BBM-2040B depending on the isolation procedure used. As used herein and in the claims, the term "BBM-2040" refers to the BBM-2040 antibiotic in either the methanol-adduct form or the desmethanol form.

The BBM-2040 antibiotics of the present invention inhibit the activity of various gram-positive and acid-fast bacteria. In addition they inhibit the growth of mammalian tumors such as P388 leukemia in mice. The new antibiotics, therefore, may be used as antibacterial agents or as antitumor agents for inhibiting mammalian tumors.

DESCRIPTION OF THE DRAWINGS

FIG. 3 shows the PMR spectrum of BBM-2040A in pyridine-$d_5$ (60 MHz).

FIG. 4 shows the PMR spectrum of BBM-2040B in pyridine-$d_5$ (60 MHz).

FIG. 5 shows the ultraviolet absorption spectrum of BBM-2040A in acetonitrile, 0.1N HCl-acetonitrile (1:9 v/v) and 0.1N NaOH-acetonitrile (1:9 v/v).

FIG. 6 shows the ultraviolet absorption spectrum of BBM-2040B in acetonitrile, 0.1N HCl-acetonitrile (1:9 v/v) and 0.1N NaOH-acetonitrile (1:9 v/v).

DETAILED DESCRIPTION

Figure 1:
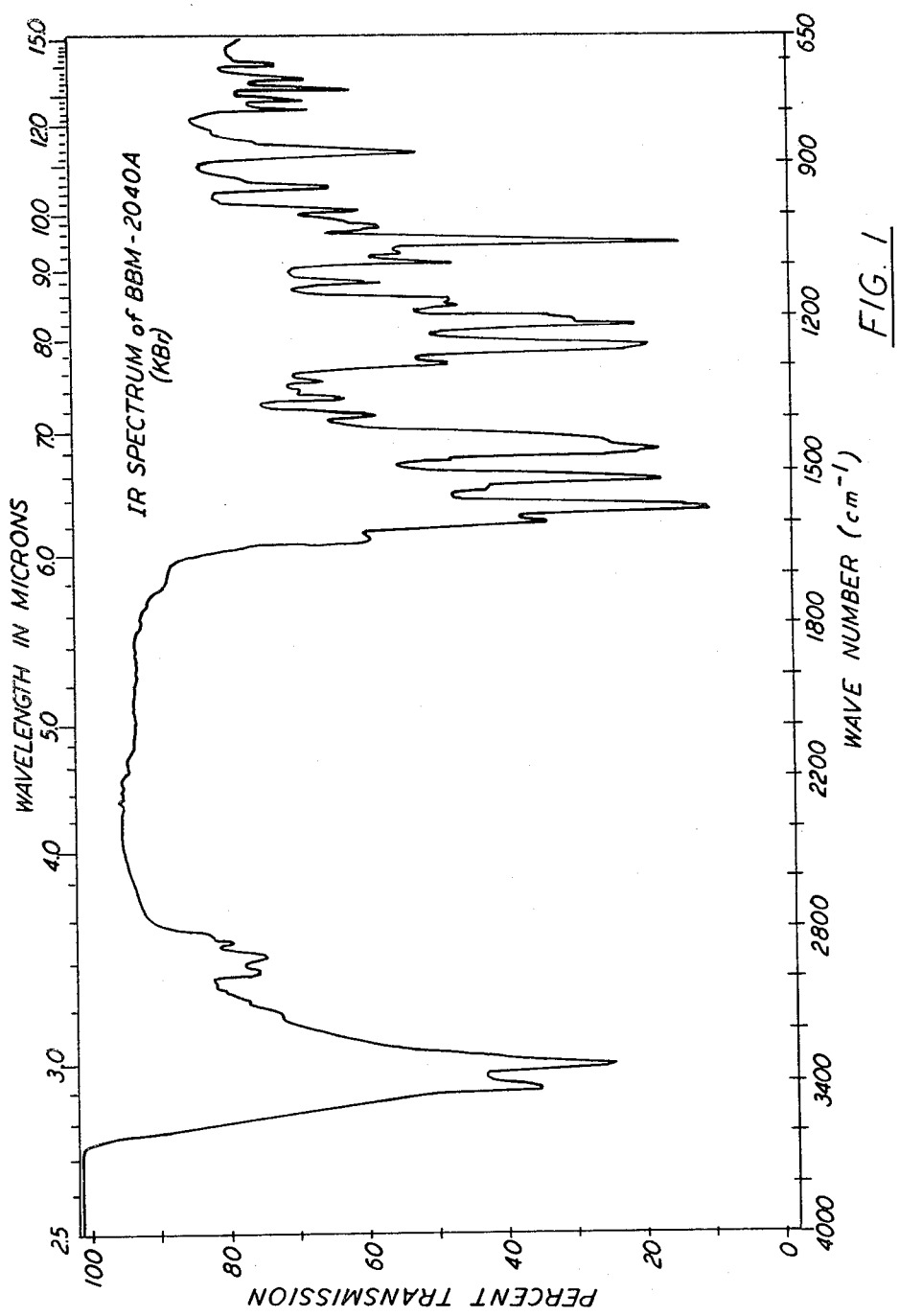
FIG. 1 shows the infrared absorption spectrum of BBM-2040A (KBr pellet).
Figure 2:
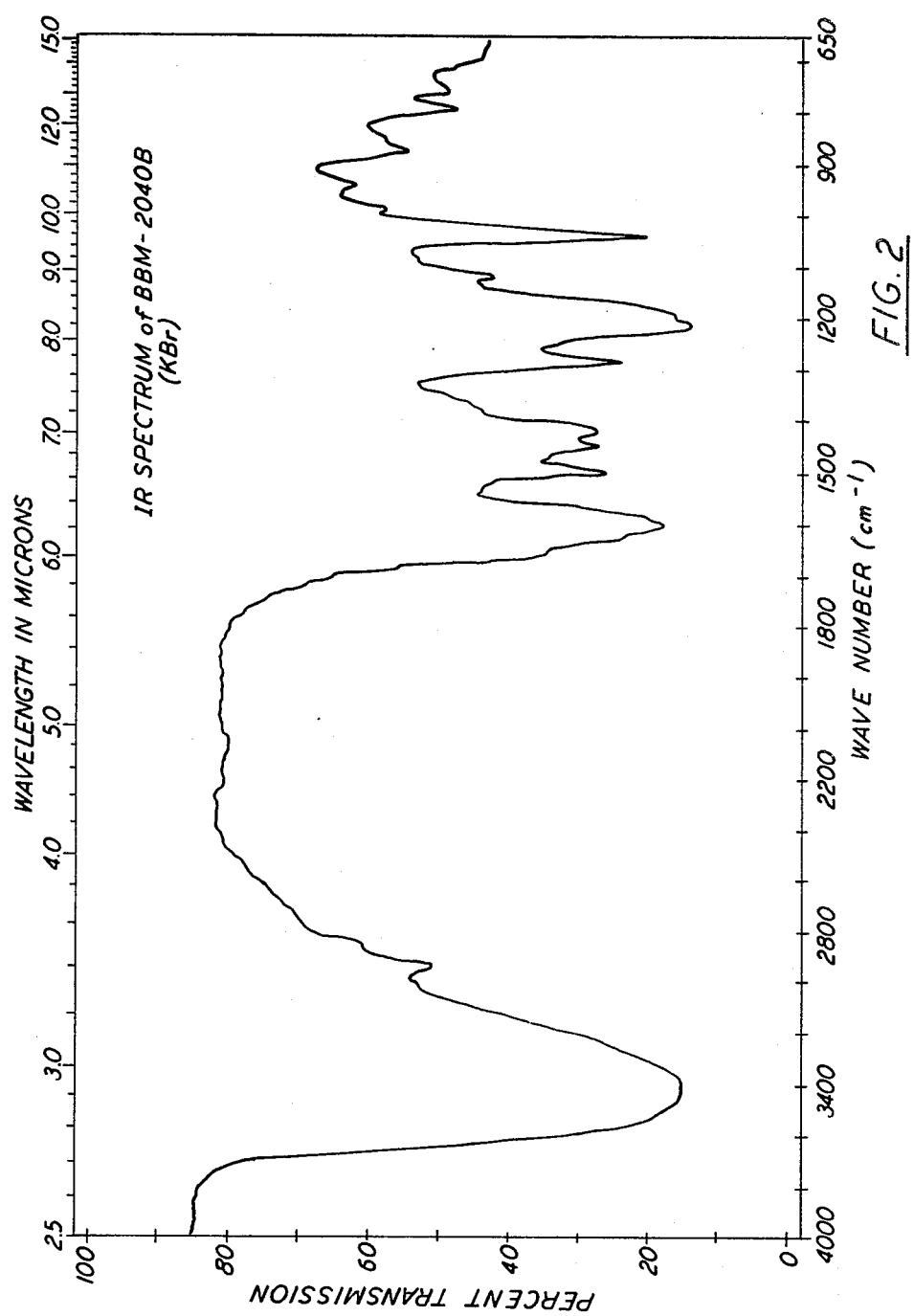
FIG. 2 shows the infrared absorption spectrum of BBM-2040B (KBr pellet).

This invention relates to novel antitumor antibiotics designated herein as BBM-2040A and BBM-2040B and to their preparation by fermentaion of a new strain of Streptomyces designated Streptomyces sp. strain J576-99. The above-mentioned producing organism was isolated from a soil sample collected in Puerto Chicama, Peru. A biologically pure culture of the organism has been deposited with the American Type Culture Collection, Washington, D.C., and added to its permanent collection of microorganisms as ATCC 39143.

The Microorganism

The actinomycete strain No. J576-99 was isolated from a soil sample and prepared by conventional procedures as a biologically pure culture for characterization. Strain J576-99 produces long, branched, aerial mycelium (0.5 μm in width) which is not fragmented. Spore-chains are formed monopodially or at the hyphal tip of the aerial mycelium. Short, straight or hooked spore-chains containing 3 to 10 spores in a chain are produced on organic agar media such as Bennett's agar and oatmeal agar. Long, irregularly coiled, open-spiralled or flexuous spore-chains containing 10–40 spores in a chain are formed on chemically defined media such as Czapek's sucrose-nitrate agar. Tight coils or loops at the tip of the spore-chain are often observed as a compact globose body. After maturation, a bead-like intermittent spore arrangement is commonly observed. The spores are spherical, oval or elliptical in shape (0.6–1.0×0.6–1.5 μm) and have a smooth surface. Sporangium, motile spore and sclerotium are not produced.

Strain J576-99 grows well on ISP media and other commonly used media. Aerial mycelia are formed abundantly on Czapek's sucrose-nitrate agar, inorganic salts-starch agar and Bennett's agar, but poorly on yeast extract-malt extract agar and oatmeal agar. The mass color of aerial mycelium is white to yellowish white. Substrate mycelia are yellowish to light brown. Melanoid and other diffusible pigment are not produced. Temperature for moderate growth ranges from 20° C. to 47° C. No growth is seen at 50° C. It is highly tolerant to sodium chloride and grows at NaCl concentration of 15% or less. The cultural and physiological characteristics of strain J576-99 are shown in Tables 1 and 2, respectively. The pattern of carbohydrate utilization by the strain is shown in Table 3.

TABLE 1

Cultural characteristics of strain No. J576-99

| | | |
|---|---|---|
| Tryptone-yeast extract broth (ISP No. 1) | G | moderate growth and formation of floccose, pale yellow pellets |
| Sucrose-nitrate agar (Czapek's agar) | G | abundant |
| | R | yellowish white (92) to moderate yellowish brown (77) |
| | A | abundant, white (263) to yellowish white (92) |
| | D | none |
| Glucose-asparagine agar | G | poor |
| | R | yellowish white (92) |
| | A | none |
| | D | none |
| Glycerol-asparagine agar (ISP No. 5) | G | moderate |
| | R | yellowish white (92) to grayish yellow (90) |
| | A | moderate, white (263) to yellowish white (92) |
| | D | none |
| Inorganic salts-starch agar (ISP No. 4) | G | abundant |
| | R | pale yellow (89) to moderate olive brown (95) |
| | A | abundant, white (263) to yellowish white (92) |
| | D | none |
| Tyrosine agar (ISP No. 7) | G | abundant |
| | R | yellow white (92) to moderate yellowish brown (77) |
| | A | moderate, white (263) to yellowish white (92) |
| | D | none |
| Nutrient agar | G | poor to moderate |
| | R | yellowish white (92) to pale yellow (89) |
| | A | poor, white (263) to yellowish white (92) |
| | D | none |
| Yeast extract-malt extract agar (ISP No. 2) | G | abundant |
| | R | pale yellow (89) to dark orange yellow (72) |
| | A | poor to moderate, white (263) |
| | D | moderate yellowish brown (77) |
| Oatmeal agar (ISP No. 3) | G | poor to moderate |
| | R | yellowish white (92) |
| | A | poor, white (263) |
| | D | none |
| Bennett's agar | G | abundant |
| | R | dark orange yellow (72) to moderate yellowish brown (77) |
| | A | abundant, white (263) to yellowish white (92) |
| | D | none |
| Peptone-yeast extract-iron agar | G | poor to moderate |

TABLE 1-continued

Cultural characteristics of strain No. J576-99

| | | |
|---|---|---|
| (ISP No. 6) | R | grayish yellow (90) |
| | A | poor, white (263) to yellowish white (92) |
| | D | light olive brown (94) |

*observed after incubation at 28° C. for 3 weeks
**Abbreviation: G = growth; R = reverse color; A = aerial mycelium; D = diffusible pigment
***Color and number in parenthesis follow the color standard in "Kelly, K. L. & D. B. Judd: ISCC-NBS color-name charts illustrated with Centroid Colors. U.S. Dept. of Comm. Cir. 553, Washington, D.C., Nov., 1975".

TABLE 2

Physiological characteristics of strain No. J576-99

| Test | Response | Method and medium |
|---|---|---|
| Range of temperature for growth | Maximal growth at 28° C. to 43° C. Moderate growth at 20° C. and 47° C. No growth at 10° C. and 50° C. | Bennett's agar |
| Gelatin liquefaction | Liquefied. | Glucose-peptone-gelatin medium |
| Starch hydrolysis | Hydrolyzed. | Starch agar plate |
| Reactions in skimmed milk | Not coagulated and not peptonized. | Difco skimmed milk |
| Formation of melanoid pigment | Not produced. | Tyrosine agar, peptone-yeast-iron agar and tryptone-yeast extract broth |
| Nitrate reduction | Negative | Czapek's glucose-nitrate broth and glucose-yeast extract broth |
| pH tolerance | Growth at pH 5.0 to 10. No growth at 4.5 | Yeast extract-malt extract agar |
| NaCl tolerance | Highly tolerant. Growth at 15% or less. | 1% yeast extract, 2% soluble starch, 1.5% agar |
| Lysozyme tolerance | Highly tolerant. Growth at 0.1, 0.01, 0.001, and 0.0001%. | Trypticase soy broth plus 1.5% agar |

TABLE 3

Utilization of carbon sources by strain J576-99

| | |
|---|---|
| Glycerol | + |
| D(−)-Arabinose | + |
| L(+)-Arabinose | + |
| D-Xylose | + |
| D-Ribose | + |
| L-Rhamnose | + |
| D-Glucose | + |
| D-Galactose | + |
| D-Fructose | + |
| D-Mannose | + |
| L(−)-Sorbose | − |
| Sucrose | + |
| Lactose | + |
| Cellobiose | + |
| Melibiose | − |
| Trehalose | + |
| Raffinose | + |
| D(+)-Melezitose | − |
| Soluble starch | + |
| Cellulose | − |
| Dulcitol | − |
| Inositol | + |
| D-Mannitol | + |
| D-Sorbitol | + |
| Salicin | + |

Basal medium: Pridham-Gottlieb's inorganic medium Observed after incubation at 28° C. for 3 weeks.

Purified cell-wall of strain J576-99 contains LL-diaminopimelic acid and glycine, and the whole cell hydrolyzate contains ribose and mannose but lacks other diagnostic sugars. The chemical composition of strain J576-99 indicates that it belongs to the actinomycete of cell-wall Type I.

Although the spore and spore-chain morphology of strain J576-99 resembles that of non-streptomycetes genera such as Actinomadura, the cultural and physiological characteristics of strain J576-99 and its Type I cell-wall composition indicate that strain J576-99 might be classified as belonging to the genus Streptomyces. According to the descriptions of *Bergey's Manual* (8th ed., 1974), strain J576-99 should be placed in the species group, *spirales*, white series, non-chromogenic and smooth spore surface, which includes 17-species. Based on the ISP (International Streptomyces Project) species descriptions, strain J576-99 resembles *S. albus*, *S. almquisti*, *S. cacaoi* and *S. rangoon* in its predominant formation of short spore-chains, but differs in the carbon source utilization pattern. the carbohydrate utilization pattern of strain J576-99 is similar to that of *S. herbescens* and *S. orchraceiscleroticus*, but differences are seen in that *S. herbescens* has green-colored substrate mycelium and *S. orchraceiscleroticus* forms white, yellow, red or gray aerial mycelium and Chainia type sclerotium. Thus, strain J576-99 is considered to be a new species of the species group 17.41f (*Bergey's Manual*, 8th ed.).

It is to be understood that for the production of the BBM-2040 antibiotics, the present invention, though described in detail with reference to the particular strain Streptomyces sp. strain J576-99 (ATCC 39143), is not limited to this microorganism or to microorganisms fully described by the cultural characteristics disclosed herein. It is specifically intended that the invention embraces strain J576-99 and all natural and artificial BBM-2040-producing variants and mutants thereof.

Antibiotic Production

The BBM-2040 antibiotics of the present invention may be prepared by cultivating a BBM-2040-producing strain of the genus Streptomyces, preferably a strain of Streptomyces sp. having the identifying characteristics of ATCC 39143 or a variant or mutant thereof, in a conventional aqueous nutrient medium containing known nutritional sources for actinomycetes, i.e. assimilable sources of carbon and nitrogen plus optional inorganic salts and other known growth factors. Submerged aerobic conditions are preferably employed for the production of large quantities of antibiotic, although for production of limited amounts, surface cultures and bottles may also be used. The general procedures used for the cultivation of other actinomycetes are applicable to the present invention.

The nutrient medium should contain an appropriate assimilable carbon source such as glycerol, arabinose, xylose, ribose, glucose, fructose, sucrose, lactose, soluble starch, mannitol or sorbitol. As nitrogen sources, ammonium chloride, ammonium sulfate, urea, ammonium nitrate, sodium nitrate, etc. may be used either alone or in combination with organic nitrogen sources such as peptone, meat extract, yeast extract, corn steep liquor, soybean powder, cotton seed flour, etc. There may also be added if necessary nutrient inorganic salts to provide sources of sodium, potassium, calcium, ammonium, phosphate, sulfate, chloride, bromide, carbonate, zinc, magnesium, manganese, cobalt, iron, and the like.

Production of the BBM-2040 antibiotics can be effected at any temperature conducive to satisfactory growth of the producing organism, i.e. ~20°-47° C., and is conveniently carried out at a temperature of around 27°-32° C. Ordinarily, optimum production is obtained in shaker flasks after incubation periods of about five days. When tank fermentation is to be carried out, it is desirable to produce a vegetative inoculum in a nutrient broth by inoculating the broth culture with a slant or soil culture or a lyophilized culture of the organism. After obtaining an active inoculum in this manner, it is transferred aseptically to the fermentation tank medium. Antibiotic production may be monitored by the paper disc-agar diffusion assay using *Bacillus subtilis* M45 [Rec⁻mutant; *Mutation Res.* 16: 165–174 (1972)] as the test organism.

Isolation and Purification

The BBM-2040 antibiotic of the present invention may be obtained from the fermentation broth in two different forms, A and B, according to the procedures used for the extraction and purification of the antibiotic. Structural studies have revealed that BBM-2040A is a methanol adduct form of BBM-2040B. Therefore, the antibiotic may be recovered in the des-methanol form (BBM-2040B) by avoiding use of methanol in the extraction and chromatographic purification procedure, while the methanol adduct form (BBM-2040A) is obtained by following the same general extraction and purification procedure, but using methanol as an extraction solvent and eluant.

Isolation of BBM-2040A: Illustrative Procedure

When fermention is complete, the harvested broth is separated into mycelial cake and broth supernatant, for example, by using filtration or centrifugation. The mycelial cake is stirred with methanol and the methanol extract then concentrated to an aqueous solution. The broth supernate is subjected to chromatographic separation, for example, by applying it to a column of a non-ionic, macroreticular polymer resin such as DIAION HP-20 (Trademark of Mitsubishi Chemical Industries, Japan) and developing with a suitable methanol-containing solvent system [e.g. n-butanol:methanol:water (2:1:1 v/v)] to elute the antibiotic activity. The active eluate may then be concentrated to an aqueous concentrate and combined with the aqueous concentrate derived from the mycelial extract. The mixture of concentrates is then washed with a solvent in which the BBM-2040 antibiotics is substantially insoluble (e.g. ethyl acetate) and extracted with a suitable solvent, e.g. n-butanol. The solvent extract may then be concentrated to provide crude BBM-2040 as a brownish solid. The impure product may be purified by dissolving in methanol and subjecting the methanolic solution to silica gel column chromatography using, for example, a mixture of ethyl acetate:methanol (9/1 v/v) as the eluent. Elution of the purified BBM-2040A may be monitored by bioassay and by UV absorption at 254 nm. Active fractions may be combined, concentrated in vacuo and lyophilized to provide substantially pure BBM-2040A. Further purification can be accomplished by repeating the chromatographic purification procedure and/or by crystallization from a suitable solvent such as methanol.

Isolation of BBM-2040B: Illustrative Procedure

When fermentation is complete, the harvested broth is separated into mycelial cake and broth supernatant, for example by using filtration or centrifugation. The mycelial cake is stirred with aqueous acetone, and insoluble materials are removed by filtration. The filtrate is then concentrated to an aqueous solution which is combined with the broth supernate and subjected to chromatographic separation, for example by passing the filtrate through a column of a nonionic, macroreticular polymer resin such as DIAION HP-20 and developing with a non-methanolic solvent such as aqueous acetone. The active eluate is then concentrated to an aqueous solution and extracted with a suitable non-methanolic solvent such as n-butanol. The solvent extract may be concentrated to a crude solid of BBM-2040B. The crude BBM-2040B may be purified by dissolving in a suitable non-methanolic solvent such as aqueous acetonitrile and subjecting such BBM-2040B solution to silica gel column chromatography using a non-methanolic eluant such as aqueous acetonitrile. Elution of the purified BBM-2040B may be monitored by bioassay and thin layer chromatography [SiO$_2$:ethyl acetate:methanol (4/1 v/v)]. Active fractions may be combined, concentrated and lyophilized to provide substantially pure BBM-2040B. Since BBM-2040B is relatively unstable in solutions, the above-described chromatographic purification procedure is preferably carried out at temperatures below room temperature, for example at about 5° C.

Physico-chemical Properties

BBM-2040A and BBM-2040B are readily soluble in methanol, ethanol, n-butanol and pyridine, slightly soluble in ethyl acetate, acetone and water and practically insoluble in benzene, chloroform and n-hexane. Both forms of the antibiotic give positive reactions with ferric chloride, Rydon-Smith and ninhydrin (weak brownish pink) reagents, but are negative to Sakaguchi, Ehrlich and anthrone reactions. Molecular formulae of $C_{14}H_{18}N_2O_5$ and $C_{13}H_{14}N_2O_4$ were assigned to BBM-2040A and B, respectively, based on the $^{13}C$—NMR and mass spectral data and microanalysis. Physico-chemical properties of BBM-2040A and B are summarized in Tables 4, 5 and 6. The IR spectra of BBM-2040A and B (in KBr pellet) are shown in FIG.'s 1 and 2.

TABLE 4

Physico-chemical properties of BBM-2040A and B

| | BBM-2040A | BBM-2040B |
|---|---|---|
| Nature | Colorless needles | White amorphous powder |
| M.p. | 161–163° C. (dec.) | 134–136° C. (dec.) |
| $[\alpha]_D^{26}$ (c 0.11, pyridine) | +350° | +552° |
| Molecular formula | $C_{14}H_{18}N_2O_5$ | $C_{13}H_{14}N_2O_4$ |
| Microanalysis | Calc'd    Found | Calc'd    Found |
| C % | 57.13      56.85 | 59.54 |
| H % | 6.16         6.16 | 5.38 |
| N % | 9.52         9.33 | 10.68 |
| Mass spectrum m/z | 294(M+), 262, 242, 219, 178, 150, 122, 86, etc. | 262(M+), 242, 150, 122, 86, etc. |

| UV spectrum: $\lambda_{max}$ in nm ($\xi$) | | |
|---|---|---|
| in CH$_3$CN | in N/10HCl.90% CH$_3$CN | in N/10NaOH.90% CH$_3$CN |

TABLE 4-continued

Physico-chemical properties of BBM-2040A and B

| BBM-2040A | 223 | (23,800) | 221 | (19,200) | 230 | (18,000) |
|---|---|---|---|---|---|---|
| | 233$^{sh}$ | (21,600) | 260$^{sh}$ | (7,900) | 254$^{sh}$ | (15,100) |
| | 256$^{sh}$ | (6,800) | 290$^{sh}$ | (2,800) | 287 | (14,000) |
| | 323 | (3,900) | 320 | (1,200) | 317 | (10,100) |
| BBM-2040B | 225 | (19,400) | 222 | (16,600) | 234 | (17,900) |
| | 234$^{sh}$ | (17,800) | 260$^{sh}$ | (7,100) | 253 | (17,300) |
| | 258$^{sh}$ | (7,400) | 290$^{sh}$ | (2,900) | 288 | (12,600) |
| | 312 | (2,900) | 323 | (1,900) | 318 | (11,300) |

TABLE 5

PMR (360 MHz) of BBM-2040A (in pyridine-d$_5$)

| Chemical shift δ (ppm) | Proton | Coupling multiplicity (J:Hz) | Assignment |
|---|---|---|---|
| 2.39 | 1H | m | H$_{1A}$ |
| 2.57 | 1H | m | H$_{1B}$ |
| 3.30 | 3H | s | C$_{11}$—OCH$_3$ |
| 3.75 | 3H | s | C$_7$—OCH$_3$ |
| 4.08 | 1H | t (8.1) | H$_{11a}$ |
| 4.14 | 1H | dd (12.0 & 5.8) | H$_{3A}$ |
| 4.48 | 1H | dd (12.0 & 6.0) | H$_{3B}$ |
| 4.53 | 1H | m | H$_2$ |
| 4.77 | 1H | d (J = 6.4) | H$_{11}$ |
| 6.34 | 1H | d (J = 7.4) | C$_2$—OH |
| 6.88 | 1H | s | H$_9$ |
| 7.94 | 1H | d (J = 6.4) | N$_{10}$—H |
| 8.17 | 1H | s | H$_6$ |
| 11.68 | 1H | s | C$_8$—OH |

TABLE 6

$^{13}$C-NMR of BBM-2040A (in pyridine-d$_5$)

| Carbon | Chemical shift (δ: ppm) | Multiplicity on off-resonance |
|---|---|---|
| 1 | 25.0 | t |
| 2 | 43.4 | d |
| 3 | 41.9 | t |
| 5 | 151.7 | s |
| 5a | 126.8* | s |
| 6 | 90.0 | d |
| 7 | 137.5 | s |
| 8 | 150.1 | s |
| 9 | 101.6 | d |
| 9a | 125.4* | s |
| 11 | 73.4 | d |
| 11a | 53.3 | d |
| 7-OCH$_3$ | 41.4** | q |
| 11-OCH$_3$ | 38.9** | q |

*,**: Assignments may be interchangeable.

The PMR spectrum of BBM-2040A (FIG. 3, 60 MHz, pyridine-d$_5$) involves two OCH$_3$ groups (δ: 3.30 and 3.75 ppm), one high-field methylene group (δ: 2.1 ppm), five protons at around δ: 3.9–4.8 ppm and two aromatic protons (δ: 6.82 and 8.10 ppm), along with one NH (δ: 7.84 ppm) and two OH (δ: 6.2 and 11.50 ppm) signals. The PMR spectrum of BBM-2040B lacks the signals of higher-field OCH$_3$ and NH protons observed with BBM-2040A, while a double bond proton (δ: 8.24 ppm) is present in the spectrum of BBM-2040B. The physico-chemical properties of BBM-2040A and B described above are similar to those of neothramycin and tomaymycin, the 1,4-benzodiazepine group of antibiotics. However, the antibiotics are readily distinguished by their TLC behavior (Table 7) and PMR spectra. BBM-2040A and B cannot be differentiated by the three TLC systems examined.

TABLE 7
TLC of BBM-2040 A and B and related antibiotics

| Solvent system | BBM-2040A | BBM-2040B | Neothramycin | Tomaymycin |
|---|---|---|---|---|
| Ethyl acetate-methanol (4:1) | 0.29 | 0.29 | 0.48 & 0.40 | 0.51 |
| Chloroform-methanol (5:1) | 0.24 | 0.24 | 0.42 & 0.32 | 0.52 |
| Ethyl acetate-acetonitrile (1:1) | 0.02 | 0.02 | 0.14 & 0.08 | 0.18 |

Structures of BBM-2040 A and B

The UV absorption spectra of BBM-2040A and B resemble those of neothramycin and tomaymycin, suggesting they are similar in the chromophore structure. The mass spectrum of BBM-2040A showed a base peak at m/z 262 ($M^+$—$CH_3OH$) which was the same as the molecular ion of BBM-2040B and neothramycin. Common ion peaks (m/z 242, 219, 178, 150, 122, 86, etc.) were observed in the mass spectra of BBM-2040A, BBM-2040B and neothramycin, indicating that the structures of BBM-2040A and B are closely related to neothramycin. The spectral data and physico-chemical properties of BBM-2040A and B indicated that BBM-2040B should be the desmethanol form of BBM-2040A. This was proved by the fact that BBM-2040B was prepared from BBM-2040A in a good yield when BBM-2040A was treated with pyridine at room temperature. The following structural studies were performed mostly on BBM-2040A.

On acetylation in pyridine, BBM-2040A afforded di-O-acetyl-desmethanol derivative (II, $M^+$; m/z 346), which was consistent with the PMR data indicating the presence of two acylable hydroxyl groups in BBM-2040A. The same acetylation product was obtained by acetylation of BBM-2040A. II was treated with m-chloroperbenzoic acid at $-20°$ C. to give an oxo-compound III ($M^+$: m/z 362). Acid hydrolysis of III with 6N HCl at 105° C. for 20 hours afforded 4-hydroxy-5-methoxyanthranilic acid (IV) and cis-4-hydroxy-L-proline (V).

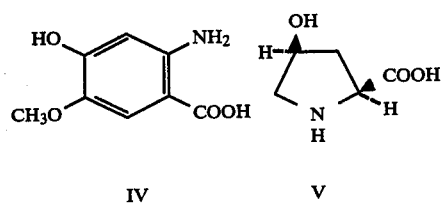

IV     V

Based on the above information along with the first order analysis of 360 MHz spectrum of BBM-2040A (Table 5), the structure of BBM-2040A was determined to be as shown below.

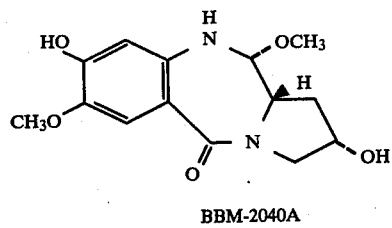

BBM-2040A

In the PMR spectrum of BBM-2040A, the signals assignable to two aromatic protons, one NH, one phenolic hydroxy and two $OCH_3$ groups are very similar to the corresponding signals of tomaymycin determined under the same condition. The proton on the carbinolamine carbon ($H_{11}$) resonated as a doublet which collapsed into a singlet upon irradiation at δ: 7.94 ppm (NH). The lack of coupling between $H_{11}$ and $H_{11a}$ observed for BBM-2040A has also been reported for the anthramycin-tomaymycin group of antibiotics having "R"-configuration at $C_{11}$ and "S" at $C_{11a}$. Thus, the 1,4-benzodiazepine part of BBM-2040A should be identical with that of tomaymycin. The alcoholic hydroxyl proton of BBM-2040A was observed at δ: 6.34 ppm as a doublet. Decoupling experiment revealed that the proton was coupled with a methine proton at δ: 4.53 ppm ($H_2$), which in turn was coupled with high-field methylene protons $H_{1A}$ and $H_{1B}$ (δ: 2.39 and 2.57), and also with a proton at δ: 4.14 ppm ($H_{3A}$). Irradiation of either of the non-equivalent methylene protons converted a triplet-proton at δ: 4.08 ($H_{11a}$) into a doublet and caused a significant change of the splitting pattern of $H_2$ proton. These PMR data are consistent with the assignment that the secondary hydroxyl group of BBM-2040A is located at C-2 of the pyrrolidine ring.

The CMR spectrum of BBM-2040A demonstrated the presence of 14 carbons (Table 6), whose assignments were made on the basis of off-resonance decoupling experiment and in comparison with the literature data of neothramycin.

Thus, the structure of BBM-2040A was determined to be (2S, 11aS)-5,10,11,11a-tetrahydro-2,8-dihydroxy-7,11-dimethoxy-5-oxo-1H-pyrrolo(2,1-c) (1,4)benzodiazepine and that of BBM-2040B to be its desmethanol form as shown below.

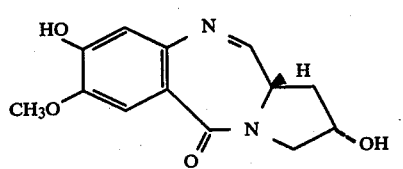

BBM-2040B

Biological Properties of BBM-2040A and B

The minimum inhibitory concentration (MIC) of BBM-2040 was determined for a variety of gram-positive, gram-negative and acid-fast bacteria by the serial two-fold agar dilution method. Nutrient agar medium was used for gram-positive and gram-negative organisms and No. 1001 medium (3% glycerol, 0.3% sodium L-glutamate, 0.2% peptone, 0.31% $Na_2HPO_4$, 0.1% $KH_2PO_4$, 0.005% ammonium citrate, 0.001% $MgSO_4$ and 1.5% agar) for acid-fast organisms. As shown in Table 8, BBM-2040 A and B showed weak antibacterial activity against *Streptococcus pyogenes*, *Micrococcus luteus*, *Micrococcus flavus* and Mycobacterium strains. The antibacterial spectrum of BBM-2040 is similar to that of neothramycin. BBM-2040 does not induce prophage in lysogenic bacteria up to a concentration of 100 mcg/ml.

TABLE 8

Antibacterial activity of BBM-2040 A and B

| Test organisms | MIC (mcg/ml) | | |
|---|---|---|---|
| | BBM-2040 A | BBM-2040 B | Neothramycin |
| *Staphylococcus aureus* FDA 209P | >100 | >100 | >100 |
| *Staphylococcus aureus* Smith | >100 | >100 | >100 |
| *Streptococcus pyogenes* A20201 | 50 | 50 | 50 |
| *Streptococcus pyogenes* PCI 1001 | 50 | 100 | 100 |
| *Micrococcus flavus* D12 | 50 | 50 | 100 |
| *Bacillus subtilis* PCI 219 | >100 | >100 | 50 |
| *Mycobacterium smegmatis* 607 | 100 | 100 | >100 |
| *Mycobacterium phlei* D88 | 100 | 100 | >100 |
| *Escherichia coli* NIHJ | >100 | >100 | 50 |
| *Escherichia coli* Juhl | >100 | >100 | >100 |
| *Klebsiella pneumoniae* D-11 | >100 | >100 | 100 |
| *Proteus vulgaris* A9436 | >100 | >100 | 100 |
| *Pseudomonas aeruginosa* A9930 | >100 | >100 | >100 |

The antitumor activity of BBM-2040A and B was determined in mice (BDF$_1$ strain) against lymphocytic leukemia P388. Each mouse was inoculated intraperitoneally with 10$^6$ cells of tumor. Graded doses of test compounds were administered to mice intraperitoneally 24 hours after the tumor implantation. The treatments were given once daily for 9 days (qd 1→9 schedule). Neothramycin was comparatively tested as a reference compound. The results are shown in Table 9. BBM-2040A and neothramycin were similarly active in this experiment, while BBM-2040B was somewhat less active than BBM-2040A.

The acute toxicity of BBM-2040A and B was determined in mice (ddY strain) by single intraperitoneal administration, the LD$_{50}$ being 34 mg/kg and 57 mg/kg respectively. The intraperitoneal LD$_{50}$ of neothramycin has been reported to be 20-30 mg/kg.

TABLE 9

Antitumor activity against leukemia P388
T/C (%) in MST*
Dose in mg/kg/day (ip)

| | 10 | 3 | 1 | 0.3 | 0.1 | 0.03 |
|---|---|---|---|---|---|---|
| BBM-2040A | (152)* | (152) | (128) | 104 | 96 | |
| BBM-2040B | (128) | (128) | 112 | 96 | 104 | |

TABLE 9-continued

Antitumor activity against leukemia P388
T/C (%) in MST*
Dose in mg/kg/day (ip)

| | 10 | 3 | 1 | 0.3 | 0.1 | 0.03 |
|---|---|---|---|---|---|---|
| Neothramycin | — | (152) | (136) | 112 | 104 | 96 |

*ratio of median survival time of test and control animals
**circle indicates significant antitumor effect.

Antitumor activity of BBM-2040A was also demonstrated by a second experiment in which BBM-2040A was tested against P388 leukemia comparatively with neothramycin and the 2β-hydroxy epimer of BBM-2040A. In this experiment lymphatic leukemia P388 was implanted intraperitoneally into male BDF$_1$ mice at an inoculum size of 10$^6$ cells per mouse. Test compounds were dissolved in 0.9% saline containing 10% dimethylsulfoxide. Graded doses of test compounds were administered to mice intraperitoneally 24 hours after the tumor implantation, and the treatment was continued once daily for 9 days. Results of the experiment are shown below in Table 10. BBM-2040A and neothramycin were similarly active, while the 2β-hydroxy epimer of BBM-2040A was inactive at 1 mg/kg/day, the highest dose tested.

TABLE 10

Antitumor Activity against leukemia P388

| Material | Dose (mg/kg/day) | MST Days | Effect MST % T/C | Average weight change (g) | Survivors Day 5 | Day 22 |
|---|---|---|---|---|---|---|
| 2β-Hydroxy epimer of BBM-2040 A | 1 | 12.0 | 100 | +1.0 | 6/6 | 0/6 |
| | 0.3 | 11.0 | 92 | +1.8 | 6/6 | 0/6 |
| | 0.1 | 11.0 | 92 | +1.3 | 6/6 | 0/6 |
| | 0.03 | 10.5 | 88 | +1.0 | 6/6 | 0/6 |
| BBM-2040A | 10 | 19.5 | 163 | −2.2 | 6/6 | 1/6 |
| | 3 | 17.0 | 142 | +0.5 | 6/6 | 0/6 |
| | 1 | 16.0 | 133 | +1.0 | 6/6 | 0/6 |
| | 0.3 | 14.0 | 117 | +1.3 | 6/6 | 0/6 |
| | 0.1 | 12.0 | 100 | +1.5 | 6/6 | 0/6 |
| Neothramycin | 3 | 17.5 | 146 | 0.0 | 6/6 | 0/6 |
| | 1 | 17.0 | 142 | +0.5 | 6/6 | 0/6 |
| | 0.3 | 14.5 | 121 | +0.8 | 6/6 | 0/6 |
| | 0.1 | 13.0 | 108 | +1.0 | 6/6 | 0/6 |
| Control | Saline | 12.0 | — | +1.3 | 12/12 | 0/12 |

Tumor inoculum: 10$^6$ ascites cells implanted i.p.
Host: ♂ BDF$_1$ mice
Treatment: QD 1→9, i.p.
Evaluation: MST = median survival time
Effect: % T/C = (MST treated/MST control) × 100
Criteria: % T/C ≧ 125 considered as significant antitumor activity As shown above BBM-2040 A and B possess antibacterial activity against various gram-positive and acid-fast bacteria and are thus useful in the therapeutic treatment of mammals and other animals for infectious diseases caused by such bacteria. Additionally, they may be utilized for other conventional applications of antibacterial agents such as disinfecting medical and dental equipment.

The marked antitumor activity shown against P388 leukemia in mice indicate that BBM-2040A and B are also therapeutically useful in inhibiting the growth of mammalian tumors.

The present invention, therefore, provides a method for therapeutically treating an animal host affected by a bacterial infection or by a malignant tumor which comprises administering to said host an effective antibacterial or tumor-inhibiting dose of BBM-2040A or B or a pharmaceutical composition thereof.

In another aspect the present invention provides a pharmaceutical composition which comprises an effective antibacterial or tumor-inhibiting amount of BBM-2040 A or B, or a mixture thereof, in combination with an inert pharmaceutically acceptable carrier or diluent. These compositions may be made up in any pharmaceutical form appropriate for parenteral administration.

Preparations according to the invention for parenteral administration include sterile aqueous or non-aqueous solutions, suspensions or emulsions. They may also be manufactured in the form of sterile solid compositions which can be dissolved in sterile water, physiological saline or some other sterile injectable medium immediately before use.

It will be appreciated that the actual preferred amounts of the BBM-2040 antibiotic used will vary according to the particular composition formulated, the mode of application and the particular situs, host and disease being treated. Many factors that modify the action of the drug will be taken into account by those skilled in the art, for example, age, body weight, sex, diet, time of administration, route of administration, rate of excretion, condition of the host, drug combinations, reaction sensitivities and severity of the disease. Administration can be carried out continuously or periodically within the maximum tolerated dose. Optimal application rates for a given set of conditions can be ascertained by those skilled in the art using conventional dosage administration tests in view of the above guidelines.

The following examples are provided for illustrative purposes only and are not intended to limit the scope of the invention.

EXAMPLE 1

Fermentation of BBM-2040

A well grown agar slant of Streptomyces sp. strain No. J576-99 was used to inoculate seed medium containing 3.0% soybean meal, 2.0% corn starch, 1.0% $CaCO_3$ and 0.33% $MgSO_4.7H_2O$, the pH being adjusted to 7.0 before sterilization. The seed culture was incubated at 28° C. for 3 days on a rotary shaker (250 rpm) and 4 ml of the growth was transferred into a 500-ml Erlenmeyer flask which contained 100 ml of fermentation medium having the same composition as the seed medium. Fermentation was carried out on a rotary shaker at 28° C. and the antibiotic activity in the fermentation broth was determined by paper disc agar-diffusion assay using *Bacillus subtilis* M45 (a Rec⁻ mutant) as a test organism. The pH of the broth gradually rose with the progress of fermentation and reached 8.0–8.2 after 120 hours when a peak antibiotic potency of 50 mcg/ml was obtained.

EXAMPLE 2

Isolation of BBM-2040 A

The harvested broth (20 liters) prepared according to Example 1 was separated into mycelial cake and broth supernate by using a continuous centrifuge (Kokusan H-600). The mycelial cake was stirred with 3 liters of methanol for 30 minutes and the methanolic extract was concentrated to an aqueous solution (400 ml). The broth supernate was applied to a column of DIAION HP-20 (2 liters) and, after being washed with water (3 liters), the column was developed with a mixture of n-butanol-methanol-water (2:1:1 v/v) to elute the antibiotic activity. The active eluate was evaporated in vacuo to an aqueous concentrate (400 ml) and combined with the aqueous concentrate derived from the mycelial extract. The mixture was washed with two 800-ml portions of ethyl acetate and extracted with two 800-ml portions of n-butanol. The butanol extracts were combined and concentrated in vacuo to afford crude BBM-2040 as a brownish solid (6.6 grams). This solid was dissolved in a small amount of methanol and charged on a column of silica gel (Wakogel C-200, 100 grams) which was developed with a mixture of ethyl acetate-methanol (9:1 in volume). The elution was monitored by bioassay (*B. subtilis* M45) and by UV absorption at 254 nm. The chromatographic process was carried out in a cold room at 5° C. The active eluates were combined, concentrated in vacuo and lyophilized. Amorphous white solid thus obtained was crystallized from methanol to give a pure preparation of BBM-2040 A as colorless needles (1.10 grams).

EXAMPLE 3

Isolation of BBM-2040 B

The fermentation broth (50 liters) prepared according to Example 1 was centrifuged by a continuous centrifuge apparatus. The mycelial cake collected was homogenized with 80% aqueous acetone (14 liters) for 30 minutes and insoluble materials were removed by filtration. The filtrate was concentrated in vacuo to an aqueous solution which was combined with the broth supernate and passed through a column of DIAION HP-20 (2.5 liters). The column was washed with water (8 liters) and the activity eluted with 80% aqueous acetone. The combined active eluates (8 liters) were concentrated in vacuo to an aqueous solution (2 liters), which was washed with two 2-liter portions of ethyl acetate and then extracted with two 2-liter portions of n-butanol. The n-butanol extracts were combined and evaporated in vacuo to give crude solid of BBM-2040B (23.9 grams). Since BBM-2040B is relatively unstable in solutions, the chromatographic process described below was operated in a cold room (5° C.). The crude solid of BBM-2040B (23 grams) was dissolved in a small volume of aqueous acetonitrile and applied to a column of silica gel (200 g). The column was developed with 95% aqueous acetonitrile and the elution monitored by bioassay (*B. subtilis* M45) and TLC ($SiO_2$:EtOAc-MeOH=4:1 v/v). Appropriate fractions were collected and concentrated in vacuo below 35° C. and lyophilized to afford a pure sample of BBM-2040B as an amorphous white powder (3.30 grams).

We claim:

1. The process for the production of the antibiotic, BBM-2040A, having the formula

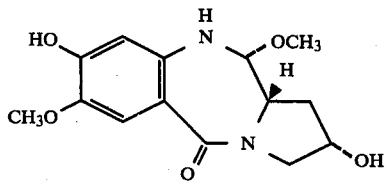

which comprises cultivating Streptomyces sp. Strain J576-99 (ATCC 39143) or a BBM-2040 producing mutant thereof in an aqueous nutrient medium containing assimilable sources of carbon and nitrogen under submerged aerobic conditions until a substantial amount of BBM-2040 is produced by said organism in said culture medium and then recovering the BBM-2040 antibiotic from the culture medium in its methanol adduct form.

2. The process for the production of the antibiotic, BBM-2040B, having the formula

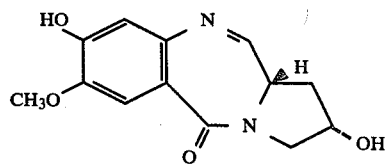

which comprises cultivating Streptomyces sp. Strain J576-99 (ATCC 39143) or a BBM-2040-producing mutant thereof in an aqueous nutrient medium containing assimilable sources of carbon and nitrogen under submerged aerobic conditions until a substantial amount of BBM-2040 is produced by said organism in said culture medium and then recovering the BBM-2040 antibiotic from the culture medium in its desmethanol form.

3. A biologically pure culture of the microorganism Streptomyces sp. ATCC 39143, said culture being capable of producing the antibiotic BBM-2040 in a recoverable quantity upon cultivation in an aqueous nutrient medium containing assimilable sources of nitrogen and carbon.

* * * * *